United States Patent [19]

Kuzuhara et al.

[11] Patent Number: 5,972,713
[45] Date of Patent: *Oct. 26, 1999

[54] METHOD FOR DETERMINING TOTAL CHLORINE AMOUNT AND A KIT FOR DETERMINING TOTAL CHLORINE AMOUNT

[75] Inventors: Noriyasu Kuzuhara; Minoru Takada; Masayuki Numa, all of Hino, Japan

[73] Assignee: Konica Corporation, Tokyo, Japan

[*] Notice: This patent issued on a continued prosecution application filed under 37 CFR 1.53(d), and is subject to the twenty year patent term provisions of 35 U.S.C. 154(a)(2).

[21] Appl. No.: 08/706,892

[22] Filed: Sep. 3, 1996

[30] Foreign Application Priority Data

Sep. 5, 1995 [JP] Japan .................................. 7-228020

[51] Int. Cl.$^6$ .................................................. G01N 21/29
[52] U.S. Cl. .......................... 436/125; 436/164; 422/61
[58] Field of Search ..................... 422/61, 50; 436/124, 436/125, 101, 164, 166

[56] References Cited

U.S. PATENT DOCUMENTS 1,986,403   1/1935   Lehmkuhl ............................. 436/125
4,092,115   5/1978   Rupe et al. ........................... 436/125
4,339,243   7/1982   Magers et al. ........................ 436/101
4,716,110  12/1987   Wada et al. ........................... 435/25
5,362,650  11/1994   Harp .................................... 436/125
5,491,094   2/1996   Ramana et al. ....................... 436/125

FOREIGN PATENT DOCUMENTS 34 43 415 A1   2/1986   Germany.

OTHER PUBLICATIONS

Derwent Publications Ltd., Class D04 AN 94–046034 of JP–A–06 003 346 (1994).

*Primary Examiner*—Jeffrey Snay
*Attorney, Agent, or Firm*—Frishauf, Holtz, Goodman, Langer & Chick, P.C.

[57] ABSTRACT

A method for determining total chlorine amount present in a sample by mixing the sample with a benzidine indicator solution comprising a benzidine compound capable of forming a dye by a reaction with a chlorine, wherein the hue of the formed dye changes depending upon the mole ratio of the chlorine to benzidine compound and determining the total chlorine amount from the hue. A kit for practicing the method incudes the indicator and a color scale for the hues of the dye.

13 Claims, 3 Drawing Sheets

FIG. 1 (a)
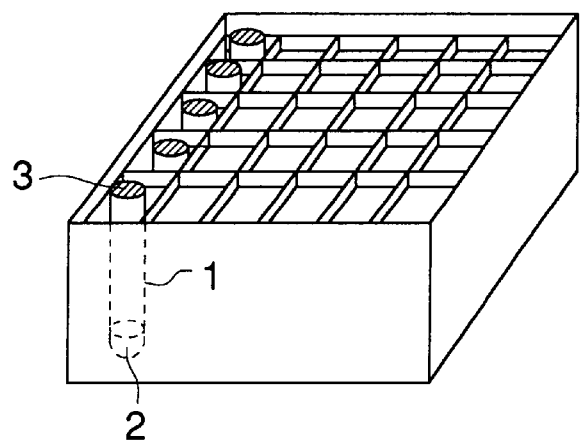
FIG. 1 (b)
FIG. 1 (c)
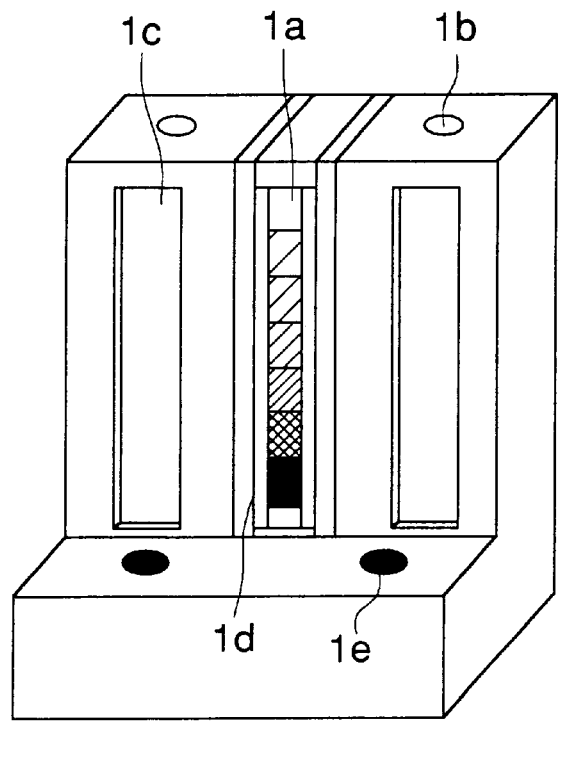
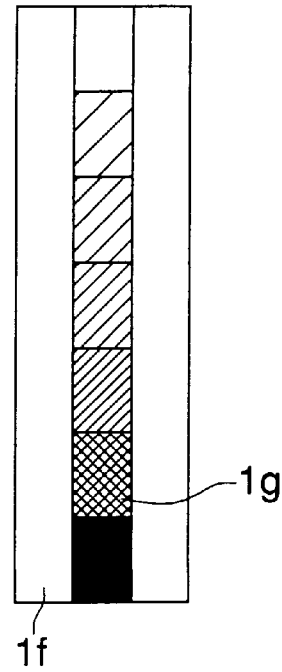

METHOD FOR DETERMINING TOTAL CHLORINE AMOUNT AND A KIT FOR DETERMINING TOTAL CHLORINE AMOUNT

FIELD OF THE INVENTION

The present invention relates to a method for determining total chlorine amount by using benzidine, tetraalkylbenzidine and, particularly 3,3',5,5'-tetramethylbenzidine (TMB), and N-sulfoalkyl-3,3',5,5'-tetramethylbenzidine (SA-TMB), and a kit for determining total chlorine amount.

BACKGROUND OF THE INVENTION

A chlorine amount denotes a hypochlorous acid, which is generated when a chlorine agent is dissolved in water and a chloroamine, which is generated when this is connected with ammonia. The former is called a free chlorine and the latter a combined chlorine. For the method of determining these chlorine amount, for example, o-tolidine colorimetric method, or is usually used. Besides these, when the chlorine amount is relatively high, iodine titration is also applied.

In the present invention, the total chlorine amount means a sum of the free chlorine amount and the combined chlorine amount.

Benzidines such as TMB and SA-TMB is a coloring substrate frequently used for determining peroxidase activity in enzyme-linked immunosorbent assay (ELISA) (for example, see Tetrahedron, volume 30, pp. 3299–3302 by Holland, and Japanese Patent O.P.I. Publication No. 52300/1986). In ELISA, in order to measure fine amounts of material existing in vivo, the following theory is commonly utilized: a binder material such as an antibody against aforesaid material is fixed on a cavity (well) of beads or special plates which are called "carriers", and then, a solution containing aforesaid material was reacted for binding. Following this, a second material (for example, an antibody) possessing binding property to aforesaid material which has been peroxidase-labeled is allowed to react and bind. Next, the TMB was added to aforesaid material under the existence of hydrogen peroxide. As a result, due to the effect of the peroxidase, hydrogen peroxide generates oxygen. As a result, the TMB is oxidized so as to make coloring. Due to this theory, the correlation between the degree of light absorbance of the coloring material and aforesaid material concentration can be utilized.

Namely, benzidine compounds such as TMB and SA-TMB are used for measuring hydrogen peroxide under the existence of peroxidase.

In accordance with JIS K0102, an o-tolidine or a DPD colorimetric method determines chlorine amount in a solution by comparing a yellow coloring of potassium chromate—potassium dichromate solution or a pink coloring of disodium 1-(4-methylbenzenesulfonamide)-7-(2-methylphenylazo)-8-hydroxy-3,6-naphthalene sulfonic acid chlorine standard solution with a dye generated due to mixture of the solution to be tested and o-tolidine or DPD.

According to this method, it is possible to precisely determine the chlorine amount. However, chlorine standard calorimetric solutions having various concentrations (for example, 20 sample tubes in which a can concentration is increased from 0.01 mg/l to 0.2 mg/l at an increment of 0.01 mg/l.) must be prepared. Since this standard solution cannot be free from color-fading, it is impossible to store for a long time. Therefore, it is necessary to be prepared when it is necessary. In addition, when precipitation occurs when preparing, preparing must be conducted again. Accordingly, its procedure is very complicated.

On the other hand, for measuring chlorine amount having relatively high concentration, an iodine titration method is used. According to JIS K 0102, in this method too, a potassium iodide solution and the solution to be tested for chlorine are mixed so that isolated iodine is titrated with sodium thiosulfate. After yellow color of the solution is thinned, a starch solution is added as an indicator. The mixed solution is titrated until blue color of starch is extinguished. By the use of the amount of sodium thiosulfate required for titration, chlorine amount can be calculated from a certain equation. However, this method is also very complicated in terms of necessitating titration operation.

Cases in which measurement of chlorine is required can be considerable in various ways. For example, in food manufacture, when a hypochlorous acid solution is used for sterilizing of pipes, tanks, etc., in the manufacturing steps of liquid foods, it is necessary for the hypochlorous acid solution to be removed by washing. However, in the process control of routine steps like this, it is extremely difficult to undergo complicated and elaborate inspections, and, as a result, it is possible for such determinations to be left to the intuition of those skilled in the art.

Concerning coloring of the TMB, Japanese Patent Examined Publication No. 25152(1990) discloses that two sequential coloring steps takes place. The two sequential coloring steps explained therein is assumed to be the first kind in blue, and, next, in the second kind in brown. This first coloring in blue tends to be only temporary, and finally changes into brown, That is to say, this indicates that blue color subsequently changes into brown with lapse of time. This reference also discloses that this phenomenon occurs more easily with higher analytical densities. However, the above-mentioned reference only refers to the existence of the first and second kinds (i.e., blue and brown colors) and the inventors attention in this patent is focused on only how to maintain the blue color, and, as regards the brown dye which subsequently appears in time, it only refers to it as being an unpreferable phenomenon. Thus, in this respect the reference does not disclose the relationship of the color hues, which change depending upon the mol ratio between the TMB and the oxidant.

In the above-mentioned o-tolidine colorimetric method, the reaction solution appears yellowish, therefore, the change of the yellow density is used only for determination of chlorine, and change of hue was not at all utilized. In addition, in accordance with Holland's method, the reacted solution appears bluish, therefore, only change of blue-density was used for determination of peroxidase activity. In Holland's method, change of hue was not utilized at all.

Accordingly, the reference neither discloses nor indicates the color changes stably in blue, green, yellow, orange or red depending on the concentration of the oxidant.

Further in TMB, when the concentration of TMB is high, there is a problem that dye (this phenomenon remarkably occurs in the case of blue color) after coloring, tends to precipitate when it is stored for a pre-determined period of time. In Japanese Patent O.P.I. Publication No. 62-182,659 (1987), it is disclosed that by making active use of the nature of certain kinds of dyes caused by specific kinds of anion compounds, said insoluble dye is used for visualizing biological substances such as dyeing of immuno-tissues, etc.

The first object of the present invention is to provide a method of determining total chlorine amount in a test solution by the use of a phenomenon in which said total chlorine reacts with benzidine compound so as to form a dye, and the formed dye changes in the hue depending upon a mol ratio of the total chlorine amount to the benzidine compound and a kit used for determining total chlorine amount, and the above-method can be carried out by simple operation and simply by observing the hue of the generated color in the test solution.

Further, the second object of the present invention is to provide a method of determining total chlorine amount, which is capable of restraining precipitation of dyes even if coexisting a benzidine compound with a chlorine, and a kit used therefore.

SUMMARY OF THE INVENTION

The above-mentioned objects of the present invention are achieved by the following items.

(1) A method for determining a total chlorine amount in a test solution by the use of the hue of a dye produced by mixing a solution containing a benzidine compound with the test solution.

(2) In a method for determining the chlorine amount in a test solution by the use of the hue of a dye produced by mixing a solution containing a benzidine compound and the test solution, wherein said method is characterized in comprising a step of changing the range of content of chlorine, by which change in the hue of the dye to be produced is caused by changing concentration of the benzidine compound.

(3) The method of determining total chlorine amount described in (1) or (2), wherein the benzidine compound is a tetraalkylbenzidine.

(4) The method of determining total chlorine amount described in (3) above, wherein said tetraalkylbenzidine is 3,3',5,5'-tetramethylbenzidine.

(5) The method of determining total chlorine amount described in (3) above, wherein said tetraalkylbenzidine is a compound represented by Formula I:

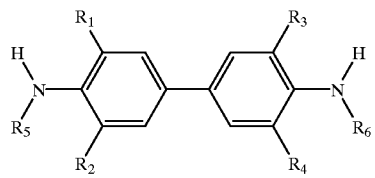

Formula I

In the Formula, $R_1$, $R_2$, $R_3$, and $R_4$ independently represent a hydrogen atom or an alkyl group having 1 through 6 carbon atoms, provided that at least three of $R_1$, $R_2$, $R_3$ and $R_4$ represent said alkyl group having 1–6 carbon atoms, and they may be either same or different; R5 and R6 independently represent a hydrogen atom or a sulfoalkyl group represented by Formula II: $-(CH_2)_nSO_3$ wherein n represents an integer of 1 to 6: provided that either one of $R_5$ and $R_6$ represents said sulfoalkyl group which may be substituted by at least one hydroxyl group.

(6) The method of determining total chlorine amount described in (4), wherein said hue of is any one of blue, green, yellow, orange or red color or any intermediate color thereof.

(7) The method of determining total chlorine amount described in (5), wherein said hue is a color selected from the group consisting of bluish-green, yellow, orange, red and intermediate color thereof.

(8) A kit for determining total chlorine amount in a test solution by the use of the hue of a dye produced by mixing a solution containing a benzidine indicator or a salt thereof and the test solution.

(9) A kit for determining total chlorine amount in a test solution by the use of the hue of a dye produced by mixing a solution containing a benzidine indicator or a salt thereof and the test solution characterized in that said solution containing a benzidine indicator or a salt thereof comprises a solution capable of diluting the benzidine indicator or the salt thereof.

(10) A kit used for determining total chlorine amount in a test solution by the use of the hue of a dye produced by mixing a solution containing a benzidine indicator or a salt thereof and the test solution characterized in that said kit comprises color samples containing names and color samples of the standard colors observed by combinations of plurality of magnification of dilution and/or concentration and total chlorine amount content in the test solution.

(11) The kit used for determining total chlorine amount described in any one of (8) through (11) above, wherein said benzidine indicator is a tetraalkylbenzidine.

(12) The kit described in (11) above, wherein said tetraalkylbenzidine indicator is a 3,3',5,5'-tetraalkylbenzidine.

(13) The kit described in (11) above, wherein said tetraalkylbenzidine indicator is a compound represented by the above-mentioned Formula I.

(14) A method for determining total chlorine amount in a test solution by the use of the hue of a dye produced by mixing a solution containing a benzidine indicator or a salt thereof, at least one compound selected from the group consisting of Formulae (1), (2), (3) and (4), and a test solution;

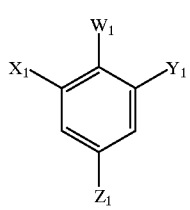

Formula (1)

wherein $W_1$ represents any one of $NO_2$, CN, CHO, $COR_7$ ($R_7$ represents an alkoxyl group or a hydroxyl group; $X_2$, $Y_1$ and $Z_1$ independently represent an $-NR_8R_9$ group; $R_8$ and $R_9$ independently represent an alkyl group or a hydrogen atom, an $-OR_{10}$ group, wherein $R_{10}$ represents an alkyl group or a hydrogen atom; an alkyl group having 1–4 carbon atoms, or Cl, F, I or H, provided that at least one of $X_1$, $Y_1$ and $Z_1$ represents an atom or a group other than hydrogen atom;

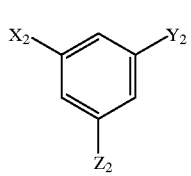

Formula (2)

wherein $X_2$, $Y_2$ and $Z_2$ independently represent an $-NR_{12}R_{13}$ group; $R_{12}$ and $R_{13}$ independently represent an alkyl group or a hydrogen atom, an $-OR_{14}$ group, wherein $R_{14}$ represents an alkyl group or a hydrogen atom; $R_{15}$ wherein $R_{15}$ represents an alkyl group of 1–4 carbon atoms, Cl, F, I or H, provided that at least one of $X_2$, $Y_2$ and $Z_2$ represents an atom or a group other than hydrogen atom:

Formula (3)

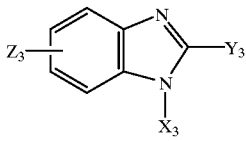

wherein $X_3$ represents an —$NR_{16}R_{17}$ group, wherein $R_{16}$ and $R_{17}$ independently represent an alkyl group, alkenyl group or alkinyl group, a phenyl group, a heterocyclic residue or a hydrogen, alkyl group having 1–4 carbon atoms, or Cl, F, I or H; $Y_3$ represents an alkyl group, alkenyl group, alkinyl group, a phenyl group; a heterocyclic group residue; an —NR20R21 group, in which $R_{20}$ and $R_{21}$ independently represent an alkyl group or a hydrogen atom; an alkylthio group, a phenylthio group, an —$OR_{22}$, in which $R_{22}$ represents an alkyl group or a hydrogen atom; $R_{23}$, in which $R_{23}$ is an alkyl group having 1–4 carbon atoms, Cl, F, I or H; $Z_3$ represents a hydroxyl group, an alkoxyl group, an alkyl group or a cycloalkyl group:

wherein $X_4$ and $Y_4$ independently represent an group selected from an alkyl group, an alkoxyl group, a phenyl group, a phenyl group substituted by a hydroxyl group or an amino group; an —$NR_{24}R_{25}$ group, in which $R_{24}$ and $R_{25}$ represents an alkyl group or a hydrogen atom.

(15) In a method of determining total chlorine amount in a test solution from hue of a dye produced by mixing a solution containing a benzidine indicator or a salt thereof and at least one compound represented by Formulae (1) through (4) above, and the test solution, wherein said method is characterized in comprising a step of changing the range of total chlorine amount, by which change in the hue of the dye to be produced is caused by changing concentration of the benzidine indicator or a salt thereof.

(16) The method of determining total chlorine amount described in (14) or (15), wherein the benzidine indicator is a tetraalkylbenzidine.

(17) The method of determining total chlorine amount described in (16), wherein the tetraalkylbenzidine is 3,3',5,5'-tetramethylbenzidine.

(18) The method of determining total chlorine amount described in (16), wherein the tetraalkylbenzidine is a derivative of 3,3',5,5'-tetraalkylbenzidine represented by said Formula I.

(19) A kit used for determining total chlorine amount in a test solution by the use of the hue of a dye produced by mixing a solution containing a benzidine indicator or a salt thereof and at least one compound selected from those represented by Formulae (1) through (4) mentioned above, and a test solution.

(20) A kit used for determining total chlorine amount in a test solution by the use of the hue of a dye produced by mixing a solution containing a benzidine indicator or a salt thereof and the test solution characterized in that said solution containing a benzidine indicator or a salt thereof, and at least one compound selected from the group consisting of by Formulae (1), (2), (3) and (4) wherein said kit comprises a solution capable of diluting said benzidine indicator or a salt thereof.

(21) A kit used for determining total chlorine amount in a test solution by the use of the hue of a dye produced by mixing a solution containing a benzidine indicator or a salt thereof, and at least one compound selected from the group consisting of Formulae (1), (2), (3) and (4) and the test solution, wherein said kit comprises color samples having standard colors observed by combinations of plurality of benzidine indicators each having different bendidine amount and total chlorine amount in said test solution.

(22) The kit used for determining total chlorine amount described in any one of (19) through (21) above, wherein said benzidine indicator is a tetraalkylbenzidine.

(23) The kit described in (22) above, wherein said tetraalkylbenzidine indicator is a 3,3',5,5'-tetraalkylbenzidine.

(24) The kit described in (22) above, wherein said tetraalkylbenzidine indicator is a compound represented by Formula I.

BRIEF DESCRIPTION OF THE DRAWINGS

FIG. 1(a) depicts a kit for sensing an oxidized product showing one example of the present invention.

FIG. 1(b) depicts a calorimeter.

FIG. 1(c) depicts a standard color scale.

DETAILED DESCRIPTION OF THE INVENTION

Figure 2:
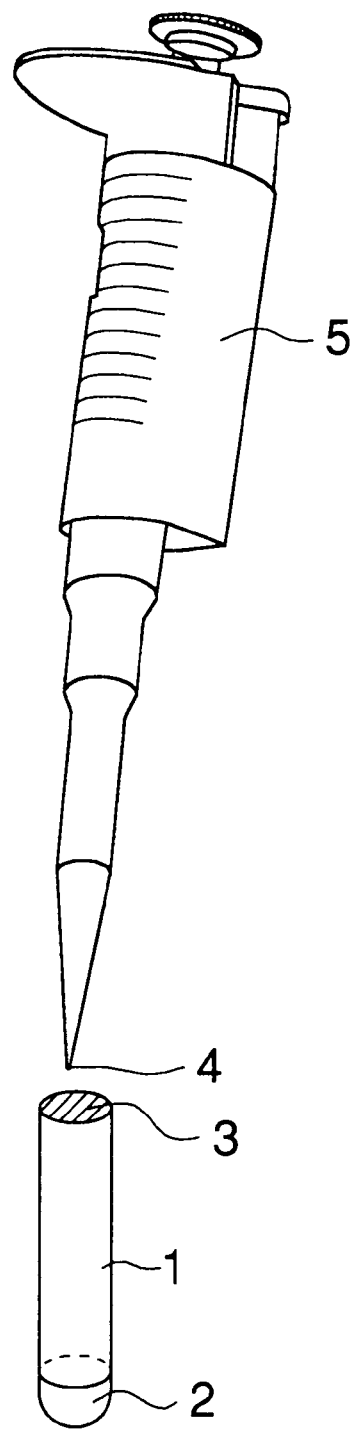
FIG. 2 is A drawing showing a container (reagent) and a injecting device (for a solution to be tested) showing one example of the present invention.

Below, the present invention is explained more in detail.

Benzidine indicator or a salt thereof is explained.

First, benzidine indicator compound represented by the above-mentioned general Formula I, which is preferably used in the present invention is explained.

In Formula I, R1, R2, R3 and R4 independently represent a hydrogen atom or a straight chain alkyl group having 1 through 6 carbon atoms, provided that at least three of $R_1$, $R_2$, $R_3$ and $R_4$ each represent said alkyl group having 1 through 6 carbon atoms, and they may be either the same or different; $R_3$ and $R_4$ independently represent a hydrogen atom or a sulfoalkyl group represented by the following Formula II: —$(CH_2)_nSO_3H$, wherein n represents an integer of 1 through 6: provided that at least one of R5 and R6 represents said sulfoalkyl group and that said sulfoalkyl group may be substituted by at least one hydroxyl group. In order to form a salt, ordinary acid is used and, for example, hydrochloride, sulfates and citrates, etc. can be mentioned.

Specific examples of the benzidine indicators are given below, however, the scope of the present invention is not limited to these.

N-(2-sulfoethyl)-3,3',5,5'-tetramethylbenzidine,
N-(3-sulfopropyl-3,3',5,5'-tetreamethylbenzidine,
N-(4-sulfobutyl)-3,3',5,5'-tetramethylbenzidine,
N-(3-sulfopropyl-3,3',5,5'-tetraethylbenzidine,
N-(2-hydroxy-3-sulfopropyl)-3,3',5,5'-tetramethylbenzidine,
N,N'-bis(2-sulfoethyl)-3,3',5,5'-tetramethylbenzidine, N,N'-bis(3-sulfopropyl)-3,3',5,5'-tetramethylbenzidine,
N,N'-bis(4-sulfobutyl)-3,3',5,5'-tetraethylbenzidine
N,N'-bis(3-sulfopropyl)-3,3',5,5'-tetraethylbenzidine,
N,N'-bis(2-hydroxy-3-sulfoethyl)-3,3',5,5'-tetramethylbenzidine,
N,N'-bis(2-hydroxy-3-sulfopropyl-3,3',5,5'-tetramethylbenzidine, For the salt of the benzidine indicator, for example, hydrochloric acid salt, sulfates, citrate of the above-mentioned compounds can be mentioned.

In the above-mentioned Formula I, in a case where $R_1$, $R_2$, $R_3$ and $R_4$ are all methyl groups, and $R_5$ and $R_6$ are hydrogen atoms, it is 3,3',5,5'-tetramethylbenzidine (TMB). Further, in a case where $R_1$, $R_2$, $R_3$ and $R_4$ are all methyl groups, $R_5$ is a sulfoalkyl group, and $R_6$ is hydrogen atom, the compound becomes to be N-sulfoalkyl-3,3',5,5'-tetramethylbenzidine (SA-TMB), both of which are preferable in the present invention. In the present invention, TMB is particularly preferable.

For one of the specific embodiments of the present invention, the case of TMB is explained as an example. First TMB is dissolved in a small amount of liquid in which TMB is soluble. The solvent used in this case may be any one as long as it can dissolve the TMB. For example, it may be either a non-protic organic solvent such as dimethyl sulfoxide (DMSO) or a protic organic solvent such as dimethyl formamide (DMF) or a lower alcohol. Also, it may be an aqueous acidic solution. Preferably, a thin aqueous solution of a mineral acid such as a diluted hydrochloric acid solution with pH 2.0 may be used.

A reagent for determining of total chlorine amount may be prepared by adding a pre-determined amount of this solution to a buffer solution. In this case, pH of the solution can be regulated within a range in which TMB is not precipitated. Preferably, it is 3 through 7, more preferably 4 through 5 and, most preferably 4.6 through 5.0. For the buffer system used herein, although there is no specific limitation, however, for example, malonic acid, phthalic acid, fumaric acid, tartaric acid, citric acid, β-alanine, dimethylglutaric acid, aspartic acid, barbituric acid, benzoic acid, succinic acid, oxalic acid, acetic acid, malic acid, 2-(N-morpholino) ethane sulfonic acid and maleic acid, etc. can be used. By adding a solution containing chlorine, for example, by adding one tenth of the total quantity of the hypochlorous acid solution, which is diluted into adequate magnification, coloration in blue, green, yellow, orange, red or an intermediate color thereof takes place, ranging from samples with lower hypochlorous acid concentration to samples of higher concentration.

To be more specific, density of coloration has a positive correlation with the concentration of hypochlorous acid with respect to the above-mentioned colors. Particularly, in blue (a range in which, concentration of hypochlorous acid with regard to the concentration of the TMB is relatively low) and orange or red (a range where concentration of hypochlorous acid with regard to the TMB concentration is relatively high), information on the concentration variation of respective colors is beneficial to the determination of the concentration of hypochlorous acid. The hypochlorous acid concentration range, in which change in the hue takes place, can be varied by controlling the concentration of TMB in the determining reagent. That is to say, by reducing the concentration of the TMB in the indicator, the concentration range of the hypochlorous acid, in which change in the hue takes place, shifts into the lower concentration range. On the contrary, by increasing the concentration of the TMB in the indicator, concentration range of the hypochlorous acid, in which change in the hue takes place can be shifted to the higher concentration range.

In other words, according to this method of observing the change of the hue, as illustrated hereinafter in the working examples, by changing the concentration of the TMB in the determining reagent, the concentration of the hypochlorous acid can be detected for example, in 10 through 200 mg/l or in 500 through 2000 mg/l. Moreover, concerning determining sensitivity, by relatively increasing the amount of the test solution to be added with respect to the determining reagent, it is, as a matter of course, possible to improve the determining sensitivity several times. In this case, for the purpose of avoiding adverse effects may caused by pH fluctuation by mixing the indicator solution and the subject solution, such as, precipitation of TMB, etc., enhancement of buffer capacity, such as by raising the concentration of the buffer solution in the determining reagent may, if necessary be made in advance.

Concerning the correlation between TMB, the chlorine amount and the hue after coloration, for example, in a case where a solution prepared by dissolving TMB in a small amount of an aqueous hydrochloric acid solution having a pH of 2.0 is added to a 0.1M citric acid –0.1M phosphoric acid buffer solution (pH 4.8) is used, coloration in the mole ratio (chlorine amount/TMB) of chlorine amount against TMB tends to be as follows:

not more than 3.0 (excluding zero); blue;

2.0 through 6: green;

3.5 through 40: yellow;

not less than 4.5; orange or red.

Herein, there are overlaps in values of the mole ratio of each coloration range. In a case where a determining reagent having a low concentration of TMB, each coloration of the above-mentioned mol ratio are as follows.

less than 2.0 (excluding zero): blue not less than 2 and less than 5: green not less than 5 and less than 20; yellow; and more than 20; red.

For example when a determining reagent solution having a high concentration of TMB is used, each coloration of the above-mentioned mol ratio are as follows:

less than 3.0 (excluding zero) blue not less than 3.0 and less than 6.0 green;

not less than 6 and less than 11 yellow; and not less than 11 red.

This indicates that each mol ratio of borders, in which hue change takes place, are different from each other depending upon the TMB concentration.

Further, the Above-mentioned results does not indicate the possibility of plurality of coloration changes take place in an identical mole ratio of one kind of a determining reagent, For example, when the TMB is used for measuring total chlorine amount, two dyes having the maximum absorbance wavelength at 655 nm and 450 nm respectively are generated.

Since their generation ratio is changed due to the mol ratio of the total chlorine amount to TMB, the hue changes between blue, green, yellow, orange and red in this order.

Particularly in the range of 10 through 50 mg/l of TMB concentration, within which determination by hue change may easily be carried out, the coloration with respect to the mol ratio is as follows:

less than 3,0 blue;

not less than 3,0 and less than 6.0 green;

not less than 6.0 and less than 10.0 yellow and
not less than 10.0: red;
provided that there is a possibility that this relation tends to be affected by the composition of said reaction solution.

Moreover, in a case where a method of determining based on hue change is not used, it is possible to apply a method of determining by concentration difference in the blue color using a determining reagent having a relatively high concentration TMB. Further, in the method of determining by the above-mentioned hue change, particularly, in the range where the concentration of the hypochlorous acid is lower than the range in which the change of the hue takes place, the use of a method of determining the concentration of the hypochlorous acid by concentration difference in the blue color remarkably enlarges the measurable range of chlorine amount of the subject.

As disclosed in the following examples, for example, in a case where a determining reagent containing 33 μg/ml of TMB, which is relatively a higher concentration, is used, when the measurable range of the hypochlorous acid concentration is 200 through 1000 mg/l, combining with the method of determination based on the blue color concentration, the measurable range of the chlorine amount is enlarged to 2 through 1,000 mg/l. This is particularly useful for the determination of a test solution, of which chlorine amount is unknown at all. That is to say, when a test solution, of which chlorine amount is unknown is tested as the primary measurement, and in the case when the concentration is out of the measurable range by the hue change, approximate concentration range of the test solution can be estimated by a bright value of formed dye (for example, blue) of the test solution of which chlorine amount is unknown, and, thus, the estimated chlorine amount may be detected by a subsequent measurement by the use of a determining reagent solution, with which measurement of the chlorine amount can be performed based on the change of coloration. Thus, for example, the measurable range may be adjusted by adjusting the concentration of the TMB in the determining reagent.

This considerably contribute to release the experimenters from useless preparation of various kinds of diluted solutions and from a complexity of performing various tests.

After the test solution is added to the determining reagent solution, since the coloration progresses rapidly, observation can be performed immediately after the coloration becomes uniform by lightly shaking or agitating the reaction solution for the purpose of preventing uneven coloration. In addition, since the generated dye can exist stably for at least several hours, observation can be performed one hour after generation thereof.

Further, with respect to the TMB, in the case where the concentration of the TMB in the determining reagent is high, there is a problem that dyes (this is particularly remarkable in blue) tend to form precipitation when they are left alone for a pre-determined period of time. In Japanese Patent O.P.I. Publication No. 62-182659 (1987), it is disclosed that making an active use of the nature that certain kinds of anions wherein generated dyes tend to change insoluble dyes with the certain kinds of anions, said insoluble dyes are used for visualization of biological substances such as for dyeing of immuno tissues.

However, in the present invention, insolubilization of dyes (precipitation formation after color forming) may be detrimental rather than helpful for the objects of the present invention. Unless there is a factor to lower extremely the solubility, this kind of precipitation formation is not generally observed after lapse of a certain period of time, which is sufficient to carry out determination after coloration. however, insolubilization of dyes is often observed, particularly with high concentration blue dyes.

After intensive research and investigation for the improvement of this point, the present inventors have found that precipitation formation can be restrained effectively by adding specified aromatic compounds, specified dicarbonyl compounds or specified benzimidazole compounds.

As the result, for example, by making these compounds coexistent, determination of total chlorine amount becomes possible even after the lapse of the time of 24 hours.

Particularly, quantitative determination by visual observation of color concentration, or by measurement of absorbance becomes possible.

In the case of a material having oxidizing ability as chlorine, the similar determination method disclosed in the present invention can be applied.

Below, the compounds represented by the general Formulae (1) through (4) are explained.

In the general Formula (1), $W_1$ represents either one of $NO_2$, CN, CHO, or $COR_7$ ($R_7$ represents an alkoxyl group or a hydroxyl group); $X_1$, $Y_1$ and $Z_1$ independently represent an $NR_8R_9$ group (wherein $R_8$ and $R_9$ independently represent an alkyl group or a hydrogen atom), $OR_{10}$ group (wherein $R_{10}$ represents an alkyl group or a hydrogen atom); alkyl group having one to four carbon atoms, Cl, F, I or H; provided that at least one of $X_1$, $Y_1$ and $Z_1$ is an atom or a group other than hydrogen atom.

In Formula (2), X2, Y2 and Z2 independently represent an $NR_{12}R_{13}$ group (wherein $R_{12}$ and $R_{13}$ independently represent an alkyl group or a hydrogen atom); $OR_{14}$ group (wherein $R_{14}$ represents an alkyl group or a hydrogen tom); an alkyl group having one to four carbon atoms or Cl, F, I or H; provided that at least one of X2, Y2 and Z2 is an atom or a group other than hydrogen atom.

In Formula (3), $X_3$ represents a $NR_{16}R_{17}$ group wherein $R_{16}$ and $R_{17}$ independently represent an alkyl group, alkenyl group, alkinyl group; a phenyl group; a heterocyclic residual group or a hydrogen atom; an $OR_{18}$ group wherein $R_{18}$ represents an alkyl group or a hydrogen atom; an alkyl group of one to four carbon atoms; or Cl, F, I and H; $Y_3$ represents alkyl group, alkenyl group, alkinyl group; phenyl group; a heterocyclic residual group; an $NR_{20}R_{21}$ group (wherein $R_{20}$ and $R_{21}$ independently represent an alkyl group or a hydrogen atom; an alkylthio group, a phenylthio group, an $OR_{22}$ group (wherein $R_{22}$ represents an alkyl group or a hydrogen atom; $R_{23}$ (wherein $R_{23}$ represents an alkyl group having one to four carbon atoms, Cl, F, I or H; $Z_3$ represents a hydroxyl group, an alkoxy group, an alkyl group, or a cycloalkyl group.

For the heterocyclic group, for exam[pal, a heterocyclic residual group such as a pyridine group, a thiophene group, a furan group, tetrahydropyran group, etc. can be mentioned.

In the above-mentioned groups of Formulae 1 to 3, the above-mentioned groups may be substituted with a hydroxyl group, an amino group, a nitrile group, a sulfonic acid group, etc.

In Formula (4), X4 and Y4 independently represent an alkyl group, an alkoxyl group, a phenyl group, and an $NR_{24}R_{25}$ group, wherein $R_{24}$ and $R_{25}$ independently represent an alkyl group or a hydrogen atom.

Below, specific exemplified compounds represented by Formulae (1) through (4) are given, However the scope of the present invention is not limited by these.

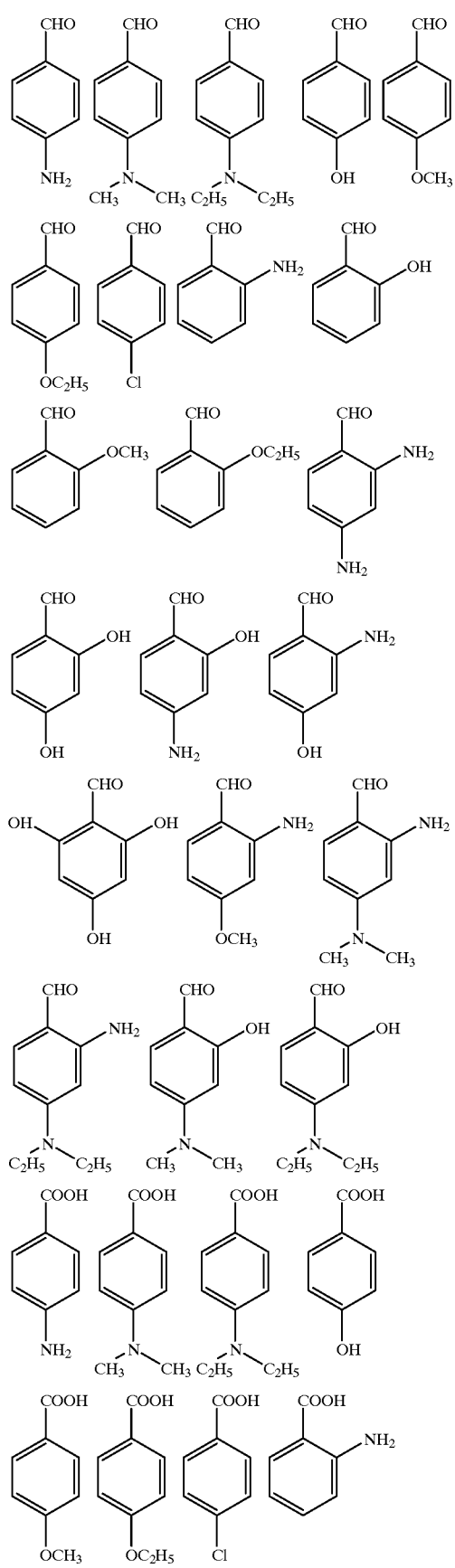
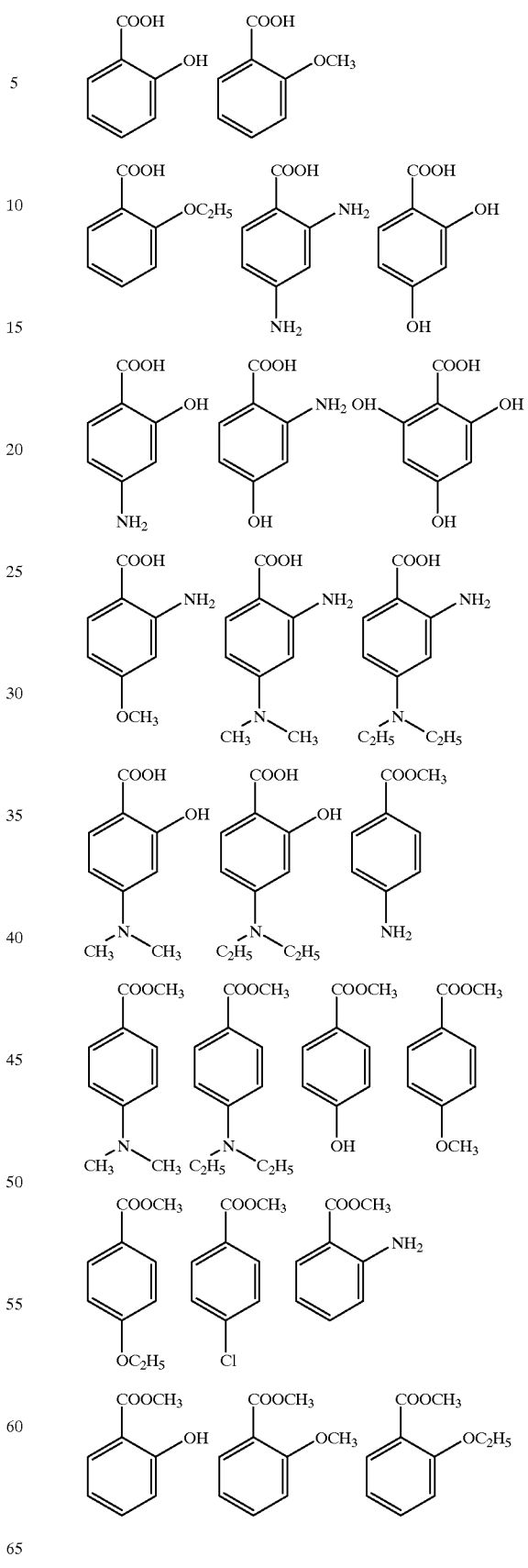

-continued

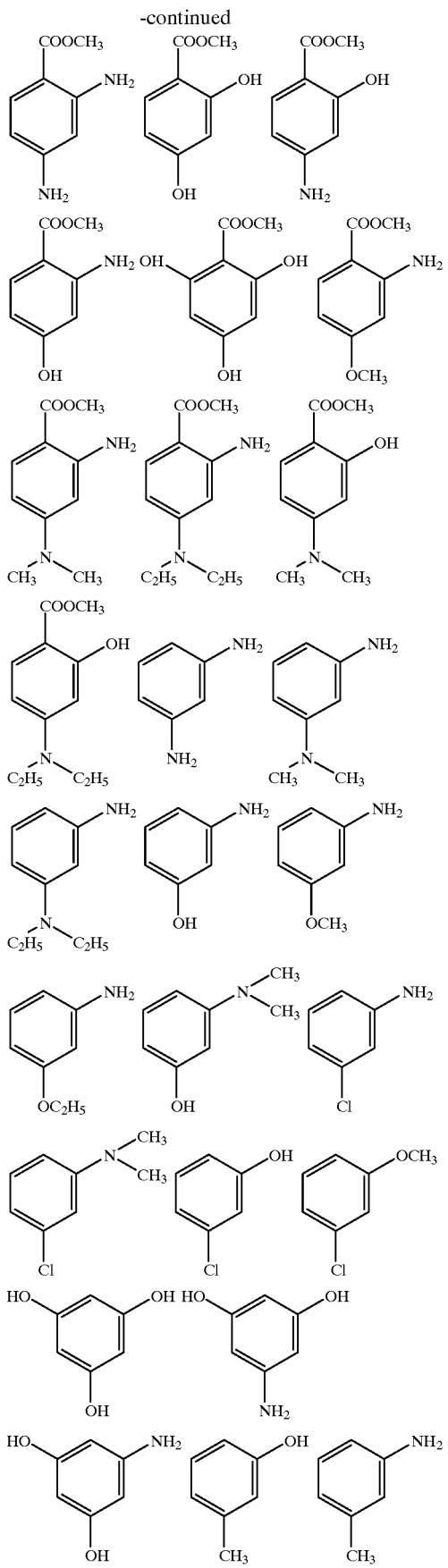

-continued

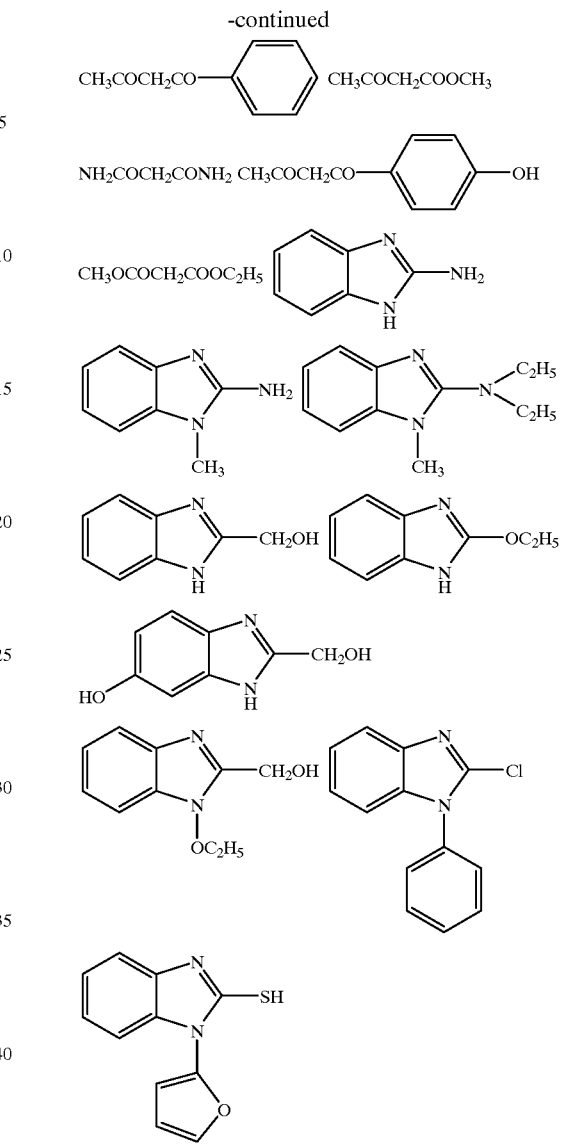

These compounds may be coexisted in any form as long as they are coexistent in the above-mentioned TMB solution at the time of the coloring reaction. For example, a test solution containing the TMB and a test solution containing any of the above mentioned compounds of the present invention may be packaged separately, and they are mixed at the time of experiments, or they may be supplied in the form they are mixed in advance. The amount of the compound of the present invention to be coexisted with the TMB compound, is preferably not less than 0.01 with respect to the amount of the TMB in terms of mol ratio. more preferably, it is not less than 0.1 and, most preferably, not less than 1. Excessive addition may not be any obstacle in the present invention, however, problems caused by the addition of the compound per se should be taken into account.

In SA-TMB, determination of total chlorine amount, especially determination of the concentration of hypochlorous acid is also possible. In this case, what should be taken care is that coloration in the bluish green is observed in stead of coloration in the blue color, which is observed in the case where the TMB is only present. That is to say, coloration takes place from the lower concentration of chlorine amount in order, in bluish green, yellow, orange, a red and an intermediate color of these colors. Concerning other properties, concentration dependence of forming dyes, etc., since they have similar properties as in the case of the TMB, determination of the concentration of the chlorine amount based on either only coloration change or concentration difference, or both coloration change and concentration difference in combination is possible.

Further, the present inventors have found that in the case of SA-TMB, precipitation tends to form easily when the concentration is high as in the case of tetraalkylbenzidines, and that the generation of this precipitation can be restrained by adding even only a small amount of the above-mentioned certain kinds of dicarbonyl compounds or benzimidazole compounds, as well as adding a certain kind of organic solvent at a pre-determined concentration (usually not less than 5%).

As a result, by coexisting these compounds, it is possible to carry out the quantitative determination even after the lapse of the time of 24 hours, either by means of visual judgment using concentration difference in the blue color region, or measurement of absorbance.

Still further, the present invention pertains to a kit used for determining total chlorine amount using a benzidine compound, preferably, tetraalkylbenzidine compounds and, particularly preferably, using 3,3',5,5'-tetramethylbenzidine (TMB) or N-sulfoalkyl-3,3',5,5'-tetramethylbenzidine (SA-TMB).

As one of specific embodiments of the kit using benzidines, preferably tetraalkylbenzidines and, particularly preferably, 3,3',5,5'-tetramethylbenzidine (TMB) or N-sulfoalkyl-3,3',5,5'-tetramethylbenzidine (SA-TMB), for example, first dissolve the TMB in a solvent in which the TMB can be soluble, This solvent be any one as long as it can dissolve the TMB, for example, it may be either a non-protic organic solvent such as dimethyl sulfoxide (DMSO) or a protic organic solvent such as dimethyl formamide (DMF) or a lower alcohol. Also, it may be an aqueous acid solution. Preferably, a thin aqueous solution of a mineral acid such as a diluted hydrochloric acid solution having pH 2.0 may be used. For example, 5 mg of TMB may be dissolved in 1 ml of diluted aqueous hydrochloric acid having pH of 2.0.

The kit for determining the chlorine amount can be prepared by adding pre-determined amount of this solution to a buffer solution. In this case, pH of the solution may be employed within a range in which TMB is not precipitated. Preferably, the pH value is 3 through 7, more preferably 4 through 5 and, most preferably, 4.6 through 5.0. For the buffer system used herein, although there is no specific limitation, however, for example, malonic acid, phthalic acid, fumaric acid, tartaric acid, citric acid, β-alanine, dimethylglutaric acid, aspartic acid, barbituric acid, benzoic acid, succinic acid, oxalic acid, acetic acid, malic acid, 2-(N-morpholino)ethane sulfonic acid and maleic acid, etc. can be used. For a specific method of using said kit, determination of chlorine amount can be performed by adding, for example, ⅒ amount of an aqueous hypochlorous acid solution, which was diluted with water by appropriate magnification, for example, to the determining reagent solution, and visual judgment of coloration, which takes place from a lower concentration of the chlorine amount to a higher one in order, in blue, green, yellow, orange and red colors. In regard to the respective colors, there is a positive correlation between concentration of the coloring and the concentration of the hypochlorous acid and, in particular, information on the density change in blue, orange or red color is useful for the determination of the concentration of hypochlorous acid.

The kit for determining total chlorine amount of the present invention is required to contain a benzidine indicator as minimum requirement for the measurement of the total chlorine amount. Further, it is possible to improve easy-to-use of the kit of the present invention by appending for example, a pipette with which a pre-determined amount of the test solution can be measured or a substitute thereof, and a color sample, with which determination of coloration or brightness of color can be carried out more easily.

In this case, the color sample may be a dye solution or in the form of gelatinous material. Further, operational convenience can be improved when for example, color printed materials on a substrate such as a paper, are employed.

The present invention also relates to a kit for determining total chlorine amount, comprising a determining reagent and a solution for diluting said determining reagent. Measurable concentration range of chlorine amount, particularly, in a case where the measurable concentration range of the chlorine amount can be detected by a hue change, the measurable concentration range of the chlorine amount can be varied by changing the TMB concentration in the determining reagent solution. That is to say, by lowering the TMB concentration in the determining reagent solution, the measurable range of total chlorine amount, in which detectable coloration change takes place, shifts to lower concentration range, and, on the contrary, by increasing the concentration of the TMB, the measurable range in which coloration change takes place, shifts to higher concentration range. And this relation can be mentioned herein above.

Accordingly, since the TMB concentration can be varied with diluting solution provided in the above-mentioned kit, it is possible to prepare a kit which gives appropriate hue change corresponding to total chlorine amount in the solution to be tested. The above-mentioned diluting solution may be any one as long as it does not give an effect on the color forming reaction of the TMB. Preferably, it is a buffer solution or a distilled water in which TMB is dissolved the buffer solution or the distilled water. The buffer solution in which the TMB is dissolved, may comprise as a matter of course, the above-mentioned additional reagent to restrain precipitation of forming dyes. As a preferable embodiment, in the case where the determining reagent is contained in the solution in which TMB is dissolved, a solution in which said reagent is contained at the same concentration is used, when the determining reagent is not contained, a buffer solution which does not contain said reagent is used; can be mentioned. In the case of SA-TMB, a kit having similar structure can be used.

In addition, the present invention relates to a kit for determining total chlorine amount, housing plural containers wherein a benzidine indicator or a salt thereof is injected in advance and tightly sealed.

The above-mentioned kit is composed of a case containing plural containers wherein an indicator is injected in advance and tightly sealed (FIG. 1a), a color sample (color scale) (FIG. 1b) and a injecting device (for solution to be tested).

The above-mentioned benzidine indicator (for example, tetraalkylbenzidine (for example, tetramethylbenzidine (TMB), compounds represented by the above-mentioned Formula I and ortho-tolidine (OT) can be mentioned.

Among of them, 3,3',5,5'-tetramethyl benzidine (TMB) is particularly preferable.

The present invention is characterized in that the benzidine indicator is injected in advance and contained in a tightly sealed container. It is an important point to inject the indicator accurately.

In the present invention, to inject the indicator accurately means that injecting error is within ±4%.

The injecting method of the present invention means to weigh the predetermined amount of reagent in advance by the use of an accurate pipet (for example, FH-10S: a product of Hirasawa Corporation) and to measure weight by the use of an accurate weighing machine (for example, AT-250: a product of Metler).

Furthermore, in the present invention, an injection volume of a benzidine indicator is set to be 1 through 5 ml, and preferably, 1 through 2 ml.

The form of container may be anything which can be tightly sealed. However, test tube types are preferably employed.

The physical properties of the material of the container is preferably 0.01 through 0.06% in terms of moisture-absorbance property, $CO_2$:50 through 900 ml/100 $m^2$/mm/24 hr atm at 25° C. and $O_2$:50 through 350 ml/100 $m^2$/24 hr atm at 25° C. in terms of gas transmissivity. More specifically, for example, polyetyrene can be mentioned.

Any form of a lid tightly closing the container of the present invention may be used. Petcock and tape-seal types are preferable. Specifically, the tape-sealed type is preferable.

The physical property of the material of the lid is, for example, in the case of polymers such as polyethylene, polypropylene, polyvinyl chloride, polyvinylidene chloride, polytetrafluoroethylene, polyester and polyethylene terephthalate, 1.1 through 2.2 $kg/cm^2$ in terms of tensile strength, 10 through 600% in terms of extension breakage and 1.1 through 25 $kg/mm^2$ in terms of internal tearing strength.

In the case of aluminum foil, tensile strength is preferably 10 through 90 $N/mm^2$, extension breakage is preferably 2 through 45% and internal tearing strength is preferably 5 through 60 $kg/mm^2$.

The moisture absorbance property of the above-mentioned lid is preferably 0 through 9%. Its gas transmissivity is preferably $CO_2$:1.5 through 2700 ml/100 $m^2$/mm/24 hr atm at 25° C. and $O_2$:20 through 2000 ml/100 $m^2$/24 hr atm at 25° C.

The lid can be sealed onto the container by means of heat, electromagnetic waves, ultrasonic waves, laser beams or adhesive agents. When it is sealed by means of heat, electromagnetic waves, ultrasonic waves or laser beams, may be used with which the lid can be sealed to the container for 1 second at 150 through 160° C. In the case of an adhesive agent, if it is a plane adhesion, it can be sealed to resist 2 $kg/cm^2$.

In the case of the present invention, it is preferable to seal it with heat or laser beams from viewpoint of tight sealing property and producibility.

With regard to the constitution of the lid and the container of the kit for determining the indicator, the lid is preferably a complex sheet (see FIGS. 2 and 3) wherein an aluminum foil and a polymer (for example, polyethylene) and the container is preferably a test tube made of polystyrene (see FIGS. 1 and 2).

In addition, in a complex sheet wherein an aluminum foil and polymer are sealed, the thickness of polymer is preferably 1 μm through 10 μm, and aluminum is preferably 5 through 50 μm provided that aforesaid sheet is not broken by means of a chip used for injection machine which injects a solution to be tested solution (an oxidized product).

For load when breaking a sealed aluminum sheet, in the case of chip for 200 μl for a common-use injecting machine, it is sufficient to be 50 $g/m^2$ or more and 200 $g/m^2$ or more is necessary to ensure against water leakage. Aluminum sheets include one manufactured by Showa Aluminum Co., Ltd. (see FIG. 3).

In addition, the thickness of the above-mentioned test tube made by polystyrene is ordinarily 200 through 2000 μm, and preferably 600 through 1300 μm.

The kit for determining total chlorine amount of the present invention can be utilized for anything. Among them, it is suitable for determining total chlorine amount.

Next, the kit for determining total chlorine amount housing plural containers wherein an indicator is injected in advance and tightly sealed will now be explained.

A kit for determining total chlorine amount exhibiting one example of the present invention (FIG. 1) is constituted as follows. Namely, FIG. 1(a) is constituted by container 1 tightly sealed with an aluminum sheet 3 (shown in FIG. 3), wherein an indicator (a reagent: 1 ml) of the present invention is injected in container (a test tube: 12Øx75 mm).

In addition, a temperature-constant tank (a block heat, wherein temperature can constantly set to 60° C.), a spectrophotometer (capable of measuring absorbance degree of 450 nm wavelength), a calorimeter (FIG. 1(b)), a standard color scale (FIG. 1 (c)), a test tubes holder and a injection machine will be prepared.

In the case of the present kit, a calorimeter (FIG. 1(b)) and a standard color scale (FIG. 1(c)) are set. In FIGS. 1(b) and 1(c), numeral 1a represents a standard color scale, 1b represents ambient light, 1c represent a color comparison window, 1d represents a standard color scale holder, 1e represents a test tube holder, 1f represents a display about total chlorine amount and 1g represents the degree of color comparison.

How to Operate the Kit

Hold container 1 in a direction shown in FIG. 2. Using a commercially available injecting machine wherein 100 μl of a solution to be tested was injected in advance, apply load of 70 $g/m^2$ with chip 4 and break aluminum seal 3 and inject 100 μl of the solution to be tested to a reagent in container 1, and then lightly vibrate it for mixing. Next, each container is left for 10 seconds to 10 minutes at Room temperature, and then, in a calorimeter, a standard color scale is prepared in advance. By comparing color with it, total chlorine amount can be determined.

In addition, by measuring the degree of light absorbance at 450 nm wavelength using a spectro-photometer of the solution to be tested (oxidized product) can appropriately be measured by comparing total chlorine amount (for example, a chlorine calibration wave) which had been determined in advance.

Figure 3:
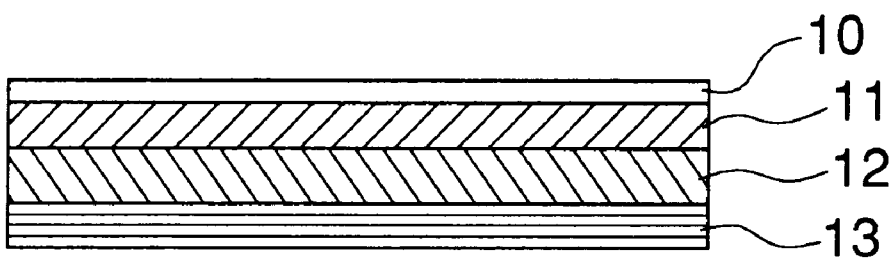
FIG. 3 is a drawing showing a cross sectional view of an aluminum sheet showing one example of the present invention.

FIG. 3 shows a cross-sectional view of an aluminum sheet (produced by Showa Aluminum Co., Ltd.) exhibiting a preferred example of the present invention.

Numeral 11 represents a protective layer, 12 represents aluminum foil, 13 represents a dry layer and 14 represents a hot melt layer capable of sealing the above-mentioned aluminum sheet onto the container of the present invention.

EXAMPLES

Below, the present invention is further explained with reference to working examples, however the scope of the present invention is not limited by these examples.

Example 1

Preparation of a reagent for determining the concentration of the remaining chlorine using TMB To prepare TMB solution, 2 ml of pH 2.0 aqueous hydrochloric acid solution was added to 10 mg of TEB (a product of Aldrich Ltd.), stirred and the TMB is dissolved. On the other hand, 0.1M citric acid/0.1M phosphoric acid buffer solution (pH of 4.8; Hereafter, refereed it to CP buffer solution) was prepared. Then, to 1 ml of this CP buffer solution, 20 µl of the TMB solution was added (to prevent precipitation formation, 1 ml of the CP buffer solution was added to 20 µl of the TMB solution), and stirred to prepare the determining reagent A. Further, by mixing the determining reagent A separately prepared, and CP buffer solution at a volume ratio of 1:2, to prepare determining reagent B, in which the TMB concentration is diluted by three times that of determining reagent A.

Further, as the same manner as the mentioned-above, the TMB concentration was diluted in this order, three times that of each determining reagents, and then, determining reagent C, in which the TMB concentration is diluted by 9 times that of determining reagent A, determining reagent D, in which the TMB concentration is diluted by 27 times that of determining reagent A and determining reagent E, in which the TMB concentration is diluted by 81 times that of determining reagent A.

Example 2
(Determination of total chlorine amount by using TMB)

Measurement of the remaining chlorine was carried out in the following manner using diluted sodium hypochlorite solutions as chlorine source. Sodium hypochlorite solution (a product of Kanto Chemical Co. Ltd.; in the following experiment, active chlorine amount is not less than 5% as a minimum requirement and each active chlorine amount in the respective solutions was calculated based on the active chlorine amount of 5%) was diluted with distilled water to prepare solutions of which total chlorine amounts were 2(mg/l), 10(mg/l), 20(mg/l), 50(mg/l), 100(mg/l), 200(mg/l), 300(mg/l), 400(mg/l), 500(mg/l), 800(mg/l), 1,000(mg/l). 2,000(mg/l) and 5,000(mg/l), respectively.

Then, 100 µl of each of the sodium hypochlorite solutions of the respective concentrations were added to glass test tubes containing 1 ml of reagent solutions A through E, and they were shaken lightly, after which coloration took place immediately. After shaking the glass tube until color became uniform, and after waiting one minute after the coloration, each hue changes were visually observed. The results are shown in Table 1.

Further, with respect to determining reagent B, particularly in the blue concentration range, absorbance at 655 nm was measured by using a spectrophotometer, Microflow Spectrophotometer Cl-750(a product of Shimazu Manufacturing Co., Ltd). The results are shown in Table 2.

TABLE 2

| Total chlorine amount (mg/l) | Color | Absorbance (650 nm) |
| --- | --- | --- |
| 2 | Slightly blue | 0.008 |
| 10 | Pale blue | 0.035 |
| 20 | Pale blue | 0.066 |
| 50 | Blue | 0.215 |
| 100 | Blue | 0.405 |
| 200 | Deep blue | 0.692 |
| 300 | Bluish green | 0.201 |
| 400 | Green | 0.061 |
| 500 | Yellow | 0.010 |
| 800 | Orange | 0.003 |
| 1000 | Red | 0.004 |
| 2000 | Red | 0.001 |
| 5000 | Red | 0.002 |

It should be understood from the results shown in Table 1 that coloration change takes place corresponding to the change of the concentration of the sodium hypochlorite solution from blue, green and yellow or red, ranging from low to high concentration of the sodium hypochlorite. Thus, it should be understood that determination of total chlorine amount can be carried out easily. Further, from this results, it is understood that determining reagent for measurement of either relatively high sensitive measurement or relatively low sensitive measurement can be prepared by adjusting the concentration range for the measurement by varying TMB concentration in the reagent solution. For example, according to the results of this example, the concentration range from 500 to 2,000 (mg/l) can be detected with determining reagent A, Similarly, the concentration range from 200 to 1,000 (mg/l) can be determined with determining reagent B, the concentration range from 20 (or 50) to 200 (mg/l) can be determined with determining reagent C, and the concentration range from 10 to 200 (mg/l) can be determined with determining reagent D respectively.

Moreover, as clearly understood from the results shown in Table 2, from the fact that there is a positive correlation

TABLE 1

| Total chlorine amount (mg/l) | Determining Reagent A | Determining Reagent B | Determining Reagent C | Determining Reagent D | Determining Reagent E |
| --- | --- | --- | --- | --- | --- |
| 2 | Slightly blue | Slightly blue | Slight blue | Approximately colorless | Approximately colorless |
| 10 | Pale blue | Pale blue | Pale blue | Pale blue | Pale bluish green |
| 20 | Pale blue | Pale blue | Blue | Pale bluish green | Pale yellow |
| 50 | Blue | Blue | Greenish blue | Pale yellow | Slightly Pale yellow |
| 100 | Blue | Blue | Green | Yellow | Yellow |
| 200 | Blue | Deep blue | Yellow | Orange | Pale orange |
| 300 | Deep blue | Deep bluish green | Orange | Orange | Pale orange |
| 400 | Deep blue | Green | Deep orange | Orange | Pale orange |
| 500 | Deep blue | Yellow | Red | Red | Pale orange |
| 800 | Deep lemon | Orange | Red | Red | Pale orange |
| 1000 | Deep yellow | Red | Red | Red | Pale orange |
| 2000 | Deep red | Red | Red | Red | Pale orange |
| 5000 | Deep red | Red | Red | Red | Pale orange | between color density and total chlorine amount, in the lower concentration region of test solutions, by observing blue color density, and in the concentration region more than the lower concentration region, by observing hue change, it is possible to determine at the concentration range of 2 through 1,000 mg/l. Furthermore, standard concentration solutions are prepared, and a calibration curve is prepared, so that it is also possible to carry out quantitative determination.

Example 3

(Preparation of a reagent for determining total chlorine amount (2) with TMB)

To prepare a TMB solution, 2 ml of pH 2.0 aqueous hydrochloric acid solution was added to 10 mg of TMB (a product of Aldrich Company), stirred well and the TMB was dissolved. On the other hand, 0.1M citric acid—0.1M phosphoric acid buffer solution (pH of 4.8) (Hereafter, denoted as CP Buffer Solution) was prepared. To this, 2,4-dihydroxybenzoic acid, 4-hydroxybenzoic acid, salicylamide, 4-aminobenzamide, 4-chlorophenol, 2-aminobenzimidazole, dimethyl malonate and ethyl 3-oxobutanate were added respectively so as to make it to prepare each solution having each final concentration of the respective compounds become two times equivalent (0.84 mM) of TMB. 20 μl of TMB solution to 1 ml CP buffer solution was added (herein, in order to avoid precipitation formation, 1 ml of CP buffer solution was added to 20 μl of TMB solution) and stirred so as to prepare determining reagents A1 through A8.

Example 4

(Determination of total chlorine amount (2) with TMB)

Measurement of the remaining chlorine was carried out in the following manner using diluted sodium hypochlorite solutions as total chlorine source. Sodium hypochlorite solution (a product of Kanto Chemical Co. Ltd.; in the following experiment, active chlorine amount is not less than 5% as a minimum requirement and each total chlorine amount in the respective solutions was calculated based on the total chlorine amount of 5%) was diluted with distilled water to prepare solutions of which total chlorine amounts were 2(mg/l), 10(mg/l), 20(mg/l), 50(mg/l), 100(mg/l), 200 (mg/l), 300(mg/l), 400(mg/l), 500(mg/l), 800(mg/l), 1,000 (mg/l). 2,000(mg/l) and 5,000(mg/l), respectively.

Then, 100 μl of each of the sodium hypochlorite solutions of the respective concentrations were added to glass test tubes containing 1 ml of reagent solutions A1 through A8, and they were shaken lightly, after which coloration took place immediately. After shaking the glass tube until color became uniform, and after waiting 24 hours after the coloration, each hue changes were visually observed. The results are shown in Table 3.

TABLE 3

| Total chlorine amount (mg/l) | Determining Reagent A | A1 | A2 | A3 | A4 | A5 | A6 | A7 | A8 |
|---|---|---|---|---|---|---|---|---|---|
| 2 | − | − | − | − | − | − | − | − | − |
| 10 | − | − | − | − | − | − | − | − | − |
| 20 | − | − | − | − | − | − | − | − | − |
| 50 | − | − | − | − | − | − | − | − | − |
| 100 | + | − | − | − | − | − | − | − | − |
| 200 | ++ | − | − | − | − | − | − | − | − |
| 300 | ++ | − | − | − | ± | − | − | ± | − |
| 400 | +++ | − | − | + | + | ± | ± | + | ± |
| 500 | +++ | − | − | + | + | ± | ± | + | ± |
| 800 | ++ | − | − | − | ± | − | − | ± | − |

TABLE 3-continued

| Total chlorine amount (mg/l) | Determining Reagent A | A1 | A2 | A3 | A4 | A5 | A6 | A7 | A8 |
|---|---|---|---|---|---|---|---|---|---|
| 1000 | − | − | − | − | − | − | − | − | − |
| 2000 | − | − | − | − | − | − | − | − | − |
| 5000 | + | − | − | − | − | − | − | − | − |

Note)
−: No precipitation is observed
±: A slight precipitation is observed
+: Precipitation is observed (The more +, the larger precipitation amount.)

From this results, it is understood that precipitation generation of dyes has been restrained after pre-determined lapse of time after coloration.

Example 5

(Preparation of a reagent for determining of total chlorine amount by using sulfopropyl-TMB)

To prepare a TMB solution, 2 ml of aqueous hydrochloric acid solution having pH of 2.0 was added to 10 mg of N-sulfopropyl-3,3',5,5'-tetramethylbenzidine (hereinafter referred to SP-TMB), stirred well and dissolved. On the other hand, 0.1M citric acid—0.1M phosphoric acid buffer solution (pH of 4.8) (hereinafter referred to as CP Buffer Solution) was prepared. To this CP buffer solution, 20 μl of the TMB solution per 1 ml CP buffer solution was added (herein, in order to avoid precipitation formation, 1 ml of CP buffer solution were added to 20 μl of SP-TMB solution), stirred so as to prepare determining reagent a. Further, by mixing the determining reagent a prepared separately and CP buffer solution at a volume ratio of 1:2. to prepare determining reagent b, in which the TMB concentration is diluted by three times that of determining reagent a.

Further, as the same manner as the mentioned-above, the TMB concentration was diluted in this order, three times that of each determining reagents, and then, determining reagent c, in which the TMB concentration is diluted by 9 times that of determining reagent a, determining reagent d, in which the TMB concentration is diluted by 27 times that of determining reagent a and determining reagent e, in which the TMB concentration is diluted by 81 times that of determining reagent a.

Example 6

(Detection of total chlorine amount by using SP-TMB)

Measurement of total chlorine amount was carried out in the following manner using diluted sodium hypochlorite solutions as chlorine source.

Sodium hypochlorite solution (a product of Kanto Chemical Co. Ltd.; in the following experiment, total chlorine amount was assumed to be 5% and total chlorine amount in the following solutions were calculated based on this assumption) was diluted with distilled water to prepare solutions of which total chlorine amounts were 2(mg/l), 10(mg/l), 20(mg/l), 50(mg/l), 100(mg/l), 200(mg/l), 300 (mg/l), 400(mg/l), 500(mg/l), 800(mg/l), 1,000(mg/l), 2,000 (mg/l) and 5,000(mg/l), respectively. Then, 100 μl of each of the sodium hypochlorite solutions of the respective concentrations were added to glass test tubes containing 1 ml of reagent solutions a through e, and they were shaken lightly, after which coloration took place immediately. After shaking the glass tube until color became uniform, and after waiting one minute after the coloration, each hue changes were visually observed. The results are shown in Table 4.

TABLE 4

| Total chlorine amount (mg/l) | Determining Reagent a | Determining Reagent b | Determining Reagent c | Determining Reagent d | Determining Reagent e |
|---|---|---|---|---|---|
| 2 | Slight bluish green | Slight bluish green | Slight bluish green | Approximately colorless | Approximately colorless |
| 10 | Pale bluish green | Pale bluish green | Pale bluish green | Pale bluish green | Pale bluish green |
| 20 | Pale bluish green | Pale bluish green | bluish green | Pale bluish green | Pale yellow |
| 50 | Bluish green | Bluish green | Bluish green | Pale yellow | Slightly pale yellow |
| 100 | Bluish green | Bluish green | Bluish green | Yellow | Yellow |
| 200 | Bluish green | Bluish green | Yellow | orange | Pale orange |
| 300 | Deep bluish green | Deep bluish green | Orange | Orange | Pale orange |
| 400 | Deep bluish green | Deep bluish green | Deep orange | orange | Pale orange |
| 500 | Deep bluish green | Yellow | Red | Red | Pale orange |
| 800 | Deep lemon color | orange | Red | Red | Pale orange |
| 1000 | Deep yellow | Red | Red | Red | Pale orange |
| 2000 | Deep red | Red | Red | Red | Pale orange |
| 5000 | Deep red | Red | Red | Red | Pale orange |

Furthermore, with respect to determining reagent a, particularly in blue concentration range), absorbance at 655 nm was measured by a Spectrophotometer, Microflow Spectrophotometer Cl-750 (a product of Shimazu Manufacturing Co., Ltd). The results are shown in Table 5.

TABLE 5

| Total chlorine amount (mg/l) | Color | Absorbance (655 nm) |
|---|---|---|
| 2 | Slight bluish green | 0.008 |
| 10 | Pale bluish green | 0.025 |
| 20 | Pale bluish green | 0.043 |
| 50 | Bluish green | 0.109 |
| 100 | Bluish green | 0.215 |
| 200 | Bluish green | 0.405 |
| 300 | Deep bluish green | 0.599 |
| 400 | Deep bluish green | 0.692 |
| 500 | Deep bluish green | 0.841 |
| 800 | Deep lemon color | 0.010 |
| 1000 | Deep yellow | 0.004 |
| 2000 | Deep red | 0.001 |
| 5000 | Deep red | 0.002 |

It should be understood from the results shown in Table 4 that coloration change takes place corresponding to the change of the concentration of the sodium hypochlorite solution from bluish-green, yellow, orange or red, in order, ranging from low to high concentration of the sodium hypochlorite. Thus, it should be understood that detection of total chlorine amount can be carried out easily. Further, from this results, it is understood that if required, determining reagent for measurement of either relatively high sensitive measurement or relatively low sensitive measurement can be prepared by adjusting the concentration range for the measurement by varying SP-TMB concentration in the reagent solution.

For example, according to the results of this example, the concentration range from 500 to 2,000 (mg/l) can be detected with determining reagent a, Similarly, the concentration range from 200 to 1,000 (mg/l) can be detected with determining reagent b, the concentration range from 20 (or 50) to 200 (mg/l) can be detected with determining reagent c, and the concentration range from 10 to 200 (mg/l) can be detected with determining reagent d respectively.

Moreover, as clearly understood from the results shown in Table 5, in the range where coloration takes place in bluish-green, there is a positive correlation between concentration of coloration and the concentration of active chlorine. Therefore, it is possible to compare total chlorine amount between plurality of test solutions.

Example 7

(Preparation of a reagent for determining total chlorine amount (2) by using SP-TMB)

To prepare a TMB solution, 2 ml of aqueous hydrochloric acid solution with pH 2,0 was added to 10 mg of SP-TMB (a product of Aldrich Company), stirred well and the TMB was dissolved. On the other hand, 0.1M citric acid—0.1M phosphoric acid buffer solution (pH of 4.8) (hereafter, refereed to CP Buffer Solution) was prepared. To this, 2,4-dihydroxybenzoic acid, 4-hydroxybenzoic acid, salicylamide, 4-aminobenzamide, 4-chlorophenol or 2-aminobenzimidazole were added respectively so as to make it to prepare each solution having each final concentration of the respective compounds become two times equivalent (0.84 mM) of SP-TMB.

CP buffer solution was added to SP-TMB solution at a ratio of 20 μl of SP-TMB solution to 1 ml of CP buffer solution, (herein, in order to avoid precipitation formation, 1 ml of CP buffer solution was added to 20 μl of SP-TMB solution) and stirred so as to prepare determining reagents a1 through a6.

Example 8

(Detection of total chlorine amount (2) by using SP-TMB)

Measurement of total chlorine amount was carried out in the following manner using diluted sodium hypochlorite solutions as active chlorine source.

Sodium hypochlorite solution (a product of Kanto Chemical Co. Ltd.; in the following experiment, total chlorine amount is not less than 5% as a minimum requirement and each active chlorine amount in the respective solutions was calculated based on total chlorine amount of 5%) was diluted with distilled water to prepare solutions of which total chlorine amounts were 2(mg/l), 10(mg/l), 20(mg/l), 50(mg/l), 100(mg/l), 200(mg/l), 300(mg/l), 400(mg/l), 500 (mg/l), 800(mg/l), 1,000(mg/l), 2,000(mg/l) and 5,000(mg/l), respectively.

Then 100 μl each of the sodium hypochlorite solutions of the respective densities were added to glass tubes containing therein 1 ml of reagent solutions a, and reagent solutions a1 through a6, and they were shaken lightly. Then, coloration took place immediately. After shaking the glass tube until color became uniform, and 24 hours after coloration, they were visually observed. Results are shown in Table 6.

Then, 100 μl of each of the sodium hypochlorite solutions of the respective concentrations were added to glass test tubes containing 1 ml of reagent solutions a through e, and they were shaken lightly, after which coloration took place immediately. After shaking the glass tube until color became uniform, and after waiting one minute after the coloration, each hue changes were visually observed. The results are shown in Table 6.

TABLE 6

| Total chlorine amount (mg/l) | Determining Reagent a | a1 | a2 | a3 | a4 | a5 | a6 |
|---|---|---|---|---|---|---|---|
| 2 | − | − | − | − | − | − | − |
| 10 | − | − | − | − | − | − | − |
| 20 | − | − | − | − | − | − | − |
| 50 | − | − | − | − | − | − | − |
| 100 | + | − | − | − | − | − | − |
| 200 | ++ | − | − | − | − | − | − |
| 300 | ++ | − | − | − | − | − | − |
| 400 | +++ | − | − | + | + | ± | ± |
| 500 | ++ | − | − | + | + | ± | ± |
| 800 | ++ | − | − | − | ± | − | − |
| 1000 | − | − | − | − | − | − | − |
| 2000 | − | − | − | − | − | − | − |
| 5000 | + | − | − | − | − | − | − |

Note)
−: No precipitation is observed
±: A slight precipitation is observed
+: Precipitation is observed Next, a standard hypochlorous acid solution was injected into test tubes wherein the above-mentioned reagent A was injected by 50 ppm, 100 ppm and 200 ppm respectively. The test tubes were vibrated lightly by hand for stirring. After leaving them for 30 seconds to 3 minutes, the change of coloring hue of the reagent corresponding to injecting error of reagent A was visually observed. Table 7 shows the results.

TABLE 7

| Injecting error | Standard | −2% | −4% | −8% | −12% |
|---|---|---|---|---|---|
| 50 ppm | Blue | Blue | Blue | Greenish blue | Bluish green |
| 100 ppm | Green | Green | Green | Yellowish green | Yellowish green |
| 200 ppm | Yellow | Yellow | Yellow | Orange | Orange |

As is apparent from Table 7, when injecting error exceeds 4%, visual hue evaluation compared to the standard hypochlorous acid resulted in notable differences.

(Errors in Injection)

1 ml of determining reagent A was injected continuously by changing operators, injecting devices and environment. Then, the weight of determining reagent A injected was measured with an accurate weighing machine. The results are as shown below.

TABLE 8

| Operator difference | Device | Environs | 1 | 2 | 3 | 4 | 5 | 6 | 7 | 8 | 9 | 10 | Mean value | Standard deviation | Fluctuation coefficient |
|---|---|---|---|---|---|---|---|---|---|---|---|---|---|---|---|
| Operator -1 | A | Laboratory | 0.986 | 0.995 | 1.089 | 1.046 | 0.998 | 0.965 | 1.065 | 0.973 | 1.036 | 1.055 | 1.0208 | 0.0427 | 4.19% |
| Operator -2 | B | Workplace X | 0.968 | 1.089 | 1.102 | 0.974 | 0.986 | 1.022 | 1.059 | 1.069 | 0.994 | 0.988 | 1.0251 | 0.0504 | 4.91% |
| Operator -3 | C | Workplace Y | 1.026 | 0.966 | 1.088 | 0.955 | 0.967 | 0.996 | 1.035 | 1.098 | 1.088 | 1.049 | 1.0268 | 0.0543 | 5.28% |

From this results it is understood that generation of precipitation of dyes has been restrained after predetected lapse of time after coloration.

Example 9
(Judgment accuracy in injecting)

Using an accurate pipet (the injecting error fluctuation coefficient must be within 1%), 1 ml of reagent A prepared in Example 1 was injected in test tubes (12×75 mm) (three bottles).

In order to detemine the influence by reaction due to injecting error, errors of −2%, −4%, −8% and −12% were set, namely reagents of 0.98 ml, 0.96 ml, 0.92 ml and 0.88 ml was prepared and injected accurately in test tubes (three bottles respectively, accordingly 12 test tubes).

From the results shown in Table 8, it should be understood that, in ordinary injecting operations, the total fluctuation coefficient due to operators, injecting devices and environment results in a range of about 5%.

Accordingly, it can be understood that, in order to optimize the performance of the kit of the present invention, reliability on evaluation accuracy can be improved by individually injecting in advance, a regent accurately.
(Storage stability tests)
1. 1 ml of reagent A was injected in test tubes made of A: polystyrene, B: acrylic, C: polyethylene and D: polypropylene respectively and by the use of an aluminum sheet as shown in FIG. 3, the test tubes were subjected to heat seal by laser light at 150 to 160° C. for one second. This sample was prepared 5 bottles.

2. In a glass wide-mouth bottle (its diameter was 8 cm), 100 ml of reagent A was poured and sealed with a petcock cap. This sample (hereinafter, referred to as bulk samples A, B and C) was prepared 3 pcs.
3. Each sample prepared as above was stored for 6 months under ordinary environmental conditions.
4. In order to check the degree of deterioration of reagent A, the degre of light absorbance at 450 nm wavelength which is a background for the reagent A was measured.

In order to observe the deterioration of coloring reaction of reagent A, 100 µl of standard hypochloric acid solution (55 ppm) was injected in 1 ml of reagent A. After leaving it for a while, the degree of light absorbance at 450 nm wavelength was measured. The following Table shows the results thereof.

TABLE 9

| Storage style | Sample | Background | Degree of light absorbance at 55 ppm |
| --- | --- | --- | --- |
| Injected and separated | A | 0.02 | 0.86 |
| Injected and separated | B | 0.02 | 0.88 |
| Injected and separated | C | 0.02 | 0.90 |
| Injected and separated | D | 0.02 | 0.83 |
| Bulk | A | 0.19 | 0.98 |
| Bulk | B | 0.20 | 1.03 |
| Bulk | C | 0.25 | 1.13 |

As is apparent from Table 9, the background of Samples A, B and C stored in a bulk state raised, showing higher value in terms of hue in coloring of reagent A compared to the actual evaluation level.

On the contrary, in reagent A of the sample stored under injecting to test tubes A, B, C and D, the rise of the background was not observed. In addition, deterioration of coloring reaction of reagent A was not also observed. It was natural that influence on density evaluation was not observed.

TMB in reagent A was replaced with OT (Orthtridine) and DPD respectively, and the same experiment as in Example 7 was conducted. As a result, the same results as in Example 7 were obtained.

What is claimed is:

1. A kit for determining total chlorine amount present in a sample, comprising:

(a) a container in which a benzidine indictor solution, comprising a benzidine compound and a buffer at a pH of 4 to 5, is stored, said benzidine compound forming a dye by a reaction with a chlorine and a hue of said dye being changed depending upon a mol ratio of said chlorine amount to said benzidine compound, (b) means for mixing said sample with a benzidine indicator solution at a pH of 4 to 5 so as to form said dye, and (c) a color scale for a calorimetric analysis having plural different sample hues wherein each of said different sample hues represents a different total chlorine amount so that said total chlorine amount of said sample is determined by comparing a hue of said dye with said plural different hues; and wherein said benzidine indicator solution comprises a benzidine compound represented by Formula I:

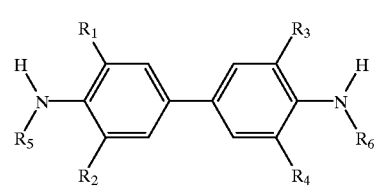

Formula I wherein, $R_1$, $R_2$, $R_3$, and $R_4$ independently represents a hydrogen atom or an alkyl group of 1 through 6 carbon atoms, provided that at least three of $R_1$, $R_2$, $R_3$, and $R_4$ represent said alkyl group, and they may be the same or different; $R_5$ and $R_6$ independently represent a hydrogen atom or a sulfoalkyl group represented by Formula II:

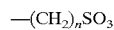

—$(CH_2)_n SO_3$            Formula II wherein n represents an integer of 1 to 6, provided that either one of $R_5$ and $R_6$ represents a sulfoalkyl group which may be substituted by at least one hydroxyl group.

2. The kit of claim 1, wherein $R_1$, $R_2$, $R_3$, and $R_4$ of said Formula I independently represents an alkyl group of 1 through 6 carbon atoms, provided that they may be the same or different.

3. The kit of claim 2, wherein $R_5$ and $R_6$ of said Formula I independently represent a sulfoalkyl group represented by said Formula II.

4. The kit of claim 1, wherein said benzidine compound is 3,3',5,5'-tetramethylbenzidine.

5. The kit of claim 1, wherein said benzidine indicator solution comprises at least one compound selected from the group consisting of Formulae 1, 2, 3 and 4:

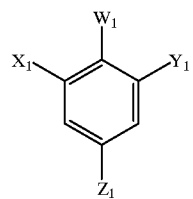

Formula 1 wherein $W_1$ represents $NO_2$, CN, CHO, $COR_7$, wherein $R_7$ represents an alkoxyl group or a hydroxyl group; $X_1$, $Y_1$ and $Z_1$ independently represent an —$NR_8R_9$ group, wherein $R_8$ and $R_9$ independently represent an alkyl group or a hydrogen atom, an —$OR_{10}$ group, wherein $R_{10}$ represents an alkyl group or a hydrogen atom), an alkyl group having 1 through 4 carbon atoms, Cl, F, I or a hydrogen atom, provided that at least one of $X_1$, $Y_1$ and $Z_1$ is an atom or a group other than a hydrogen atom:

Formula 2

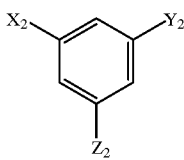

wherein $X_2$, $Y_2$ and $Z_2$ independently represent an —$NR_{12}R_{13}$ group, wherein $R_{12}$ and $R_{13}$ independently represent an alkyl group or a hydrogen atom, an —$OR_{14}$ group, wherein $R_{14}$ represents an alkyl group or a hydrogen atom, an alkyl group having 1 through 4 carbon atoms, Cl, F, I or a hydrogen atom, provided that at least one of $X_2$, $Y_2$ and $Z_2$ is an atom or a group other than a hydrogen atom:

Formula 3

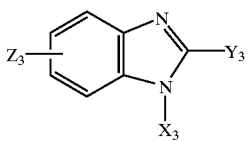

wherein $X_3$ represents an —$NR_{16}R_{17}$ group, wherein $R_{16}$ and $R_{17}$ independently represent an alkyl group, alkenyl group or alkynyl group, a phenyl group, a heterocyclic group or a hydrogen, an alkyl group having 1 through 4 carbon atoms, Cl, F, I or a hydrogen atom; $Y_3$ represents an alkyl group, alkenyl group, alkynyl group, a phenyl group, a heterocyclic group; an —$NR_{20}R_{21}$ group, wherein $R_{20}$ and $R_{21}$ independently represent an alkyl group or a hydrogen atom, an alkylthio group, a phenylthio group, an —$OR_{22}$, wherein $R_{22}$ represents an alkyl group or a hydrogen atom, an alkyl group having 1 through 4 carbon atoms, Cl, F, I or a hydrogen atom; $Z_3$ represents a hydroxyl group, an alkoxyl group, an alkyl group or a cycloalkyl group:

 Formula 4 wherein $X_4$ and $Y_4$ independently represent an alkyl group, an alkoxyl group, a phenyl group, a phenyl group substituted by a hydroxyl group or an amino group; an —$NR_{24}R_{25}$ group, wherein $R_{24}$ and $R_{25}$ represents an alkyl group or a hydrogen atom.

6. A method for determining total chlorine amount present in a sample, comprising steps of:
(a) mixing said sample with a benzidine indicator solution at a pH of 4 to 5, said benzidine indicator comprising a benzidine compound forming a dye by a reaction with a chlorine at pH of 4 to 5,
   wherein a hue of said formed dye is changed depending upon a mol ratio of said chlorine to said benzidine compound, and
(b) determining said total chlorine amount from said hue of said formed dye.

7. The method of claim 6, wherein said benzidine compound is 3,3',5,5'-tetramethylbenzidine.

8. The method of claim 6 for determining total chlorine amount present in a sample, comprising steps of:
(a) mixing said sample with a benzidine indicator solution comprising a benzidine compound capable of forming a dye by a reaction with a chlorine,
   wherein a hue of said formed dye is changed depending upon a mol ratio of said chlorine to said benzidine compound, and
(b) determining said total chlorine amount from said hue of said formed dye; and
wherein said benzidine compound is represented by Formula I:

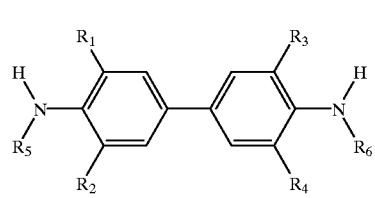 Formula I wherein, $R_1$, $R_2$, $R_3$, and $R_4$ independently represents a hydrogen atom or an alkyl group of 1 through 6 carbon atoms, provided that at least three of $R_1$, $R_2$, $R_3$, and $R_4$ represent said alkyl group, and they may be the same or different; $R_5$ and $R_6$ independently represent a hydrogen atom or a sulfoalkyl group represented by Formula II:

 Formula II wherein n represents an integer of 1 to 6, provided that either one of $R_5$ and $R_6$ represents a sulfoalkyl group which may be substituted by at least one hydroxyl group.

9. The method of claim 8, wherein $R_1$, $R_2$, $R_3$, and $R_4$ of said Formula I independently represents an alkyl group of 1 through 6 carbon atoms, provided that they may be the same or different.

10. The method of claim 9, wherein $R_5$ and $R_6$ of said Formula I independently represent a sulfoalkyl group represented by Formula II.

11. The method of claim 8, wherein said benzidine compound is 3,3',5,5'-tetramethylbenzidine.

12. The method of claim 8, wherein said benzidine indicator solution comprises at least one compound selected from the group consisting of Formulae 1, 2, 3 and 4:

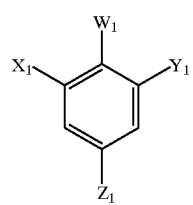 Formula 1 wherein $W_1$ represents $NO_2$, CN, CHO, $COR_7$, wherein $R_7$ represents an alkoxyl group or a hydroxyl group; $X_1$, $Y_1$ and $Z_1$ independently represent an —$NR_8R_9$ group, wherein $R_8$ and $R_9$ independently represent an alkyl group or a hydrogen atom, an —$OR_{10}$ group, wherein $R_{10}$ represents an alkyl group or a hydrogen atom), an alkyl group having 1 through 4 carbon atoms, Cl, F, I or a hydrogen atom, provided that at least one of $X_1$, $Y_1$ and $Z_1$ is an atom or a group other than a hydrogen atom:

Formula 2

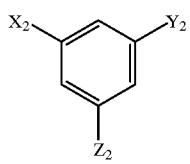

wherein $X_2$, $Y_2$ and $Z_2$ independently represent an —$NR_{12}R_{13}$ group, wherein $R_{12}$ and $R_{13}$ independently represent an alkyl group or a hydrogen atom, an —$OR_{14}$ group, wherein $R_{14}$ represents an alkyl group or a hydrogen atom, an alkyl group having 1 through 4 carbon atoms, Cl, F, I or a hydrogen atom, provided that at least one of $X_2$, $Y_2$ and $Z_2$ is an atom or a group other than a hydrogen atom:

Formula 3

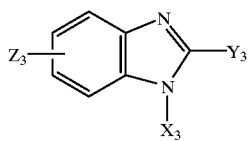

wherein $X_3$ represents an —$NR_{16}R_{17}$ group, wherein $R_{16}$ and $R_{17}$ independently represent an alkyl group, alkenyl group or alkynyl group, a phenyl group, a heterocyclic group or a hydrogen, an alkyl group having 1 through 4 carbon atoms, Cl, F, I or a hydrogen atom; $Y_3$ represents an alkyl group, alkenyl group, alkynyl group, a phenyl group, a heterocyclic group; an —$NR_{20}R_{21}$ group, wherein $R_{20}$ and $R_{21}$ independently represent an alkyl group or a hydrogen atom, an alkylthio group, a phenylthio group, an —$OR_{22}$, wherein $R_{22}$ represents an alkyl group or a hydrogen atom, an alkyl group having 1 through 4 carbon atoms, Cl, F, I or a hydrogen atom; $Z_3$ represents a hydroxyl group, an alkoxyl group, an alkyl group or a cycloalkyl group:

$$X_4—COCH_2CO—Y_4 \qquad \text{Formula 4}$$

wherein $X_4$ and $Y_4$ independently represent an alkyl group, an alkoxyl group, a phenyl group, a phenyl group substituted by a hydroxyl group or an amino group; an —$NR_{24}R25$ group, wherein $R_{24}$ and $R_{25}$ represents an alkyl group or a hydrogen atom.

13. The method of claim 8 wherein the benzidine compound is

N-(2-sulfoethyl)-3,3',5,5'-tetramethylbenzidine,

N-(3-sulfopropyl-3,3',5,5'-tetreamethylbenzidine,

N-(4-sulfobutyl)-3,3',5,5'-tetramethylbenzidine,

N-(3-sulfopropyl-3,3',5,5'-tetraethylbenzidine,

N-(2-hydroxy-3-sulfopropyl)-3,3',5,5'-tetramethylbenzidine,

N,N'-bis(2-sulfoethyl)-3,3',5,5'-tetramethylbenzidine,

N,N'-bis(3-sulfopropyl)-3,3',5,5'-tetramethylbenzidine,

N,N'-bis(4-sulfobutyl)-3,3',5,5'-tetraethylbenzidine

N,N'-bis(3-sulfopropyl)-3,3',5,5'-tetraethylbenzidine,

N,N'-bis(2-hydroxy-3-sulfoethyl)-3,3',5,5'-tetramethylbenzidine,

N,N'-bis(2-hydroxy-3-sulfopropyl-3,3',5,5'-tetramethylbenzidine, or a hydrochloric acid salt, a sulfate or a citrate of the above compounds.

* * * * *